United States Patent [19]

Miyachi et al.

[11] Patent Number: 6,071,950
[45] Date of Patent: Jun. 6, 2000

[54] N-SUBSTITUTED PYRROLIDINE DERIVATIVES AND PROCESS FOR PREPARING THE SAME

[75] Inventors: Hiroyuki Miyachi, Kazo; Masato Hoshino, Oyama; Naoki Ando, Nogi-machi; Fumiyoshi Kobayashi, Oyama, all of Japan

[73] Assignee: Kyorin Pharmaceutical Co., Ltd., Tokyo, Japan

[21] Appl. No.: 09/308,661

[22] PCT Filed: Nov. 26, 1997

[86] PCT No.: PCT/JP97/04306

§ 371 Date: Jun. 2, 1999

§ 102(e) Date: Jun. 2, 1999

[87] PCT Pub. No.: WO98/24431

PCT Pub. Date: Jun. 11, 1998

[30] Foreign Application Priority Data

Dec. 2, 1996 [JP] Japan .................................. 8-336353

[51] Int. Cl.$^7$ ..................... A61K 31/40; C07D 207/00
[52] U.S. Cl. ............................................. 514/424; 548/541
[58] Field of Search .............................. 548/541; 514/424

[56] References Cited

U.S. PATENT DOCUMENTS

| | | | |
|---|---|---|---|
| 5,686,464 | 11/1997 | Jahansson et al. | 514/315 |
| 5,776,972 | 7/1998 | Barber et al. | 514/424 |
| 5,942,537 | 8/1999 | Chamberlin et al. | 514/423 |
| 5,952,369 | 9/1999 | Ito | 514/424 |
| 5,962,504 | 10/1999 | Kozikowski et al. | 514/424 |

*Primary Examiner*—Deborah C. Lambkin
*Attorney, Agent, or Firm*—Oblon, Spivak, McClelland, Maier & Neustadt, P.C.

[57] ABSTRACT

Novel N-substituted pyrrolidine derivatives having a highly selective and potent antagonism against smooth muscle muscarine receptors and being useful for the treatment of irritable bowel syndrome and the like, characterized by being represented by general formula (1) wherein R represents a hydrogen atom, a halogen atom, or a lower alkoxy group and a process for preparing the same.

7 Claims, No Drawings

N-SUBSTITUTED PYRROLIDINE DERIVATIVES AND PROCESS FOR PREPARING THE SAME

This application is a 371 of PCT/JP97/04306 Nov. 26, 1997.

TECHNICAL FIELD

The present invention relates to novel N-substituted pyrrolidine derivatives having a highly selective and potent antagonism against smooth muscle muscarine receptors rather than cardiac muscarine receptors and being useful for the treatment of altered smooth muscle motility and tone, such as irritable bowel syndrome, diverticulosis, urinary incontinence, esophageal achalasia and chronic obstructive airway disease, and process for preparing the same.

BACKGROUND TECHNOLOGIES

As one of the therapeutic drugs for the irritable bowel syndrome, the anticholinergic agent has been used, but it brings no sufficient therapeutic effect due to, in part, deficit of tissue selectivity. Also, while compounds that was reported to have a selective antagonism against smooth muscle muscarine receptors are disclosed (Japanese Unexamined Patent Publication Nos. Hei 2-282360 and Hei 7-149640, these compounds also do not sufficiently solve the adverse effect such as mydriasis. Moreover, these compounds have diphenylalkyl moiety linked to carbon atom of the pyrrolidine ring, making them different from the structure of the inventive compounds, in which it links to the nitrogen atom of the pyrrolidine ring.

The invention is to provide novel N-substituted pyrrolidine derivatives having a highly selective and potent antagonism against smooth muscle muscarine receptors and being useful for the treatment of irritable bowel syndrome and the like.

As a result of diligent studies directed toward the development of the drug exhibiting a highly selective and potent antagonism against smooth muscle muscarine receptors and less adverse effect of mydriasis, the inventors have found that novel N-substituted pyrrolidine derivatives represented by the following general formula (1) have high safety and are useful for the treatment of irritable bowel syndrome and the like, leading to the completion of the invention.

Namely, the invention relates to N-substituted pyrrolidine derivatives represented by the general formula (1)

(1)

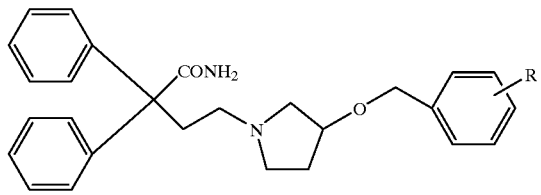

[wherein R denotes a hydrogen atom, a halogen atom or a lower alkoxy group], pharmaceutically acceptable salt, and a therapeutic drug for the irritable bowel syndrome and the like having at least one or more kinds of them as effective ingredients.

For the pharmaceutically acceptable salts of the compounds represented by the general formula (1) in the invention, acid adducts such as hydrochloride, hydrobromide, benzenesulfonate, citrate, fumarate, gluconate, lactate, maleate, methanesulfonate, succinate and tartrate are mentioned.

For the "lower alkoxy groups" in the invention, straight chain or branched ones with carbon atoms of 1 to 6 such as methoxy, ethoxy, propoxy, isopropoxy, butoxy, isobutoxy, tert-butoxy, pentoxy, isopentoxy, tert-pentoxy, neopentoxy, hexoxy, isohexoxy, sec-hexoxy and tert-hexoxy are mentioned.

For the "halogen atoms", fluorine, chlorine, bromine and iodine atoms are mentioned.

According to the invention, compounds represented by the general formula (1) can be prepared through the following process.

(1)

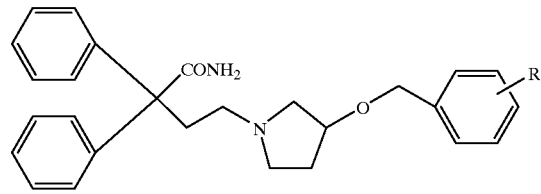

[wherein R is as described above].

Compounds having the general formula (1) can be prepared by hydrolyzing the compounds represented by the general formula (4)

(4)

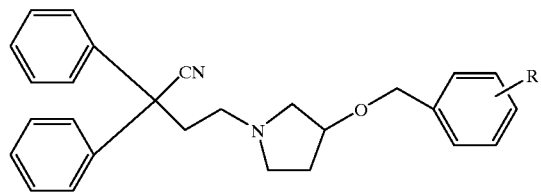

[wherein R is as described above].

In the case of the use of the acid catalyst, the hydrolysis is performed under heat, preferably at 70 to 110° C., using, for example, inorganic acid such as concentrated sulfuric acid. On the other hand, in the case of the alkali hydrolysis, it can be performed in alcohol, using, for example, alkali metal hydroxide such as sodium hydroxide or potassium hydroxide, and it is preferable to perform in refluxing tert-butanol with potassium hydroxide.

Compounds having the general formula (4) are also novel compounds and can be prepared by the reaction of the compounds represented by the general formula (3) with the compounds represented by the general formula (2), or by the reaction of the compound represented by the general formula (3) that was prepared by the deprotection of the compound represented by the general formula (3-a).

(2)

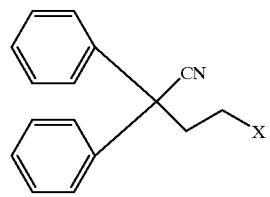

[wherein X denotes a halogen atom].

(3)

[structure: pyrrolidine with HN, 3-O-CH2-phenyl-R]

(3-a)

[structure: pyrrolidine with BocN, 3-O-CH2-phenyl-R]

[wherein R is as described above, and Boc denotes a tert-butoxycarbonyl group].

The reaction can be performed, according to normal process, by the reaction of the compounds represented by the general formula (3) with compounds represented by the general formula (2) in the presence of inorganic base or organic base, or by the treatment of the protecting group of the compounds represented by the general formula (3-a) with trifluoroacetic acid or the like and then react with the compounds represented by the general formula (2).

Compounds represented by the general formula (3) obtained by the deprotection of the compounds represented by the general formula (3-a) can be used for the next step without isolation of the deprotected product. At this time, as the bases, organic bases such as triethylamine are preferable. Moreover, for the solvents, inert solvents such as N,N-dimethylformamide, dimethyl sulfoxide and N-methyl-2-pyrrolidone can be used, but, thereamong, N-methyl-2-pyrrolidone is preferable. The reaction could be performed preferably at room temperature to 200° C., preferably at 100° C. to 150° C.

Best embodiment to put the invention into practice

In following, the invention will be illustrated based on the concrete examples, but the invention is not confined to these examples. Besides, with the compounds of the invention, there exist optical isomers based on the 3-position of the asymmetric carbon of the pyrrolidine ring, which are all included. In addition, hydrates of the compounds of the invention are all included similarly within the scope of the invention.

Besides, the abbreviations used in the invention have following meanings.
MS Mass spectrum
$^1$H-NMR Proton nuclear magnetic resonance spectrum
NMP N-methyl-2-pyrrolidone
FAB MS Fast atomic bombardment mass spectrum

EXAMPLE 1

Preparation of 4-[3-(3-chlorobenzyloxy)pyrrolidine-1-yl]-2,2-diphenylbutyronitrile To 20 ml of NMP was added 2,54 g of 4-bromo-2,2-diphenylbutyronitrile, 1.79 g of 3-(3-chlorobenzyloxy) pyrrolidine and 1.29 g of triethylamine, and the mixture was stirred for 20 hours at 140° C. The reaction mixture was concentrated under reduced pressure and water was added to the residue, and then extracted with methylene chloride. The extract was dried over anhydrous sodium sulfate. The organic layer was concentrated and the residue was purified by silica gel column chromatography (ethyl acetate) to obtain 1.81 g of the aimed compound as a brown oil.
FAB MS: 431[M+H]$^+$ EXAMPLES 2 through 4

Similarly to Example 1, the following compounds were obtained.

[structure: 2,2-diphenyl-CN compound connected via butyl chain to pyrrolidine with 3-O-CH2-phenyl-R (positions 1-6 labeled, R at position 3)]

| No. of example | R | FAB MS [M + H]$^+$ |
|---|---|---|
| 2 | H | 397 |
| 3 | 3-Cl (R form) | 431 |
| 4 | 3-Cl (S form) | 431 |

EXAMPLE 5

Preparation of 4-[3-(3-fluorobenzyloxy)pyrrolidine-1-yl]-2,2-diphenylbutyronitrile To 2.0 g of 1-tert-butroxycarbonyl-3-(3-fluorobenzyloxy) pyrrolidine was added 10 ml of trifluoroacetic acid under cooling with ice and stirring, then the mixture was stirred for 30 minutes at 0° C., then excess trifluoroacetic acid was distilled off. To the residue was added 2.0 g of 4-bromo-2,2-diphenylbutyronitrile, 2.0 g of triethylamine and 20 ml of NMP, and the mixture was stirred for 16 hours at 140° C. The reaction mixture was concentrated under reduced pressure and methylene chloride was added to the residue, then washed with water. After drying over anhydrous sodium sulfate, the organic layer was concentrated under reduced pressure and the residue was purified by silica gel column chromatography (ehtyl acetate) to obtain 0.53 g of the aimed compound as a brown oil.
FAB MS: 415[M+H]$^+$ EXAMPLES 6 through 8

Similarly to Example 5, the following compounds were obtained.

[structure: 2,2-diphenyl-CN compound connected via butyl chain to pyrrolidine with 3-O-CH2-phenyl-R]

| No. of example | R | FAB MS [M + H]$^+$ |
|---|---|---|
| 6 | 4-Cl | 431 |
| 7 | 4-F | 415 |
| 8 | 3-MeO | 427 |

EXAMPLE 9

Preparation of 4-[3-(3-chlorobenzyloxy)pyrrolidine-1-yl]-2,2-diphenylbutaneamide To 1.80 g of 4-[3-(3-chlorobenzyloxy)pyrrolidine-1-yl]2,2-diphenylbutyronitrile was added 1.41 g of potassium hydroxide and 15 ml of tert-butanol, and the mixture was refluxed for 48 hours. The reaction mixture was poured into ice water, then extracted with methylene chloride, dried over anhydrous sodium sulfate, and concentrated under reduced pressure. The residue was purified by silica gel column chromatography (methylene chloride:methanol=10:1) to obtain 1.57 g of the aimed compound as a yellow oil.

MS: 448(M$^+$)

Elemental analysis (%): As $C_{27}H_{29}ClN_2O_2.1/5H_2O$

|  | C | H | N |
|---|---|---|---|
| Calcd. | 71.65 | 6.54 | 6.18 |
| Found | 71.36 | 6.52 | 6.17 |

EXAMPLES 10 through 14

Similarly to Example 9, the following compounds were obtained.

EXAMPLE 16

Preparation of (S)-4-[3-(3-chlorobenzyloxy)pyrrolidine-1-yl]-2,2-diphenylbutaneamide Using 460 mg of 4-[3(S)-(3-chlorobenzyloxy)pyrrolidine-1-yl]-2,2-diphenylbutyronitrile obtained in Example 4, procedure was taken similarly to Example 9 to obtain 413 mg of the aimed compound as an oil.

Angle of rotation: $[\alpha]_D$: 5.1 (C=1.1, MeOH)

Elemental analysis (%): As $C_{27}H_{29}ClN_2O_2.2/5H_2O$

|  | C | H | N |
|---|---|---|---|
| Calcd. | 71.09 | 6.58 | 6.14 |
| Found | 71.00 | 6.80 | 5.92 |

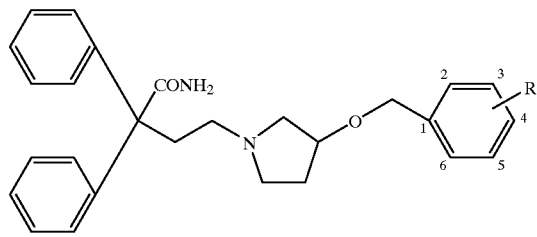

| No. of example | R | Composition formula | Property | Elemental analysis (%) Calcd./Found C | H | N |
|---|---|---|---|---|---|---|
| 10 | H | $C_{27}H_{30}N_2O_2.\frac{1}{2}H_2O$ | Amorphous | 76.57 | 7.38 | 6.61 |
|  |  |  |  | 76.89 | 7.31 | 6.56 |
| 11 | 4-Cl | $C_{27}H_{29}ClN_2O_2.H_2O$ | Amorphous | 69.44 | 6.69 | 6.00 |
|  |  |  |  | 69.38 | 6.58 | 5.83 |
| 12 | 3-F | $C_{27}H_{29}FN_2O_2.H_2O$ | Amorphous | 71.98 | 6.94 | 6.22 |
|  |  |  |  | 71.72 | 6.75 | 6.23 |
| 13 | 4-F | $C_{27}H_{29}FN_2O_2.H_2O$ | Amorphous | 71.98 | 6.94 | 6.22 |
|  |  |  |  | 71.93 | 6.84 | 6.33 |
| 14 | 3-MeO | $C_{28}H_{32}N_2O_3.\frac{3}{2}H_2O$ | Amorphous | 71.31 | 7.48 | 5.94 |
|  |  |  |  | 71.11 | 7.15 | 6.07 |

EXAMPLES 15

Preparation of (R)-4-[3-(3-chlorobenzyloxy)pyrrolidine-1-yl]-2,2-diphenylbutaneamide Using 8.93 g of (R)-4-[3-(3-chloroenzyloxy)pyrrolidine-1-yl]-2,2-diphenylbutyronitrile obtained in Example 3, procedure was taken similarly to Example 9 to obtain 7.88 g of the aimed compound as an oil.

Since this oil crystallized after standing, it was recrystallized from diisopropyl ether to obtain the aimed compound as white powdery crystals.

Melting point: 91.0~93.0° C.

Angle of rotation: $[\alpha]_D$: −5.1 (C=1.3, MeOH)

Elemental analysis (%): As $C_{27}H_{29}ClN_2O_2.2/5H_2O$

|  | C | H | N |
|---|---|---|---|
| Calcd. | 71.09 | 6.58 | 6.14 |
| Found | 71.07 | 6.42 | 6.12 |

EXPERIMENTAL EXAMPLE

1. Antagonism on the acetylcholine-induced contraction of ileum (in vitro test)

Hartley male guinea pig was killed by stunning and bleeding. The ileum was removed to make a 1.5 to 2 cm preparation. The preparation was mounted in a 10 ml organ bath filled with Tyrode's solution of 28° C. that was bubbled with 95% $O_2$/5% $CO_2$. The initial resting tension of 1 g was applied to the preparation and measurement of isomeric muscle tension was recorded.

The action of testing drug is shown in terms of $pA_2$ determined from Schild plot of the extent of right shift of the concentration-response curve on $10^{-9}M$~$3\times10^{-6}M$ of acetylcholine.

2. Antagonism on the acetylcholine-induced contraction of pupil (in vitro test)

Japanese white male rabbit was anesthetized using sodium pentobarbital and killed by bleeding. The eyeball was removed to make a preparation of sphincter muscle of the pupil. The preparation was mounted in a 10 ml organ bath filled with Krebs solution of 30° C. that was bubbled with 95% $O_2$/5% $CO_2$. The initial resting tension of 0.2 g was applied to the preparation and measurement of isometric muscle tension was recorded.

The action of testing drug is shown in terms of $pA_2$ determined from Schild plot of the extent of right shift of the concentration-response curve on $10^{-6}M \sim 10^{-2}M$ of acetylcholine.

3. Antagonism action on the acetylcholine-induced negative chronotropic action of atrium of heart (in vitro test)

Hartley male guinea pig was killed by stunning and bleeding. The heart was removed to make a preparation of atrium of heart. The preparation was mounted in a 10 ml organ bath filled with Krebs-Henseleit solution of 32° C. that was bubbled with 95% $O_2$/5% $CO_2$. The initial resting tension was made to be 0.5 g and measurement of isometric muscle tension was recorded.

The action of testing drug is shown in terms of $pA_2$ determined from Schild plot of the extent of right shift of the concentration-response curve on $10^{-9}M \sim 3 \times 10^{-6}M$ of acetylcholine.

4. Inhibitory effect in the defecation model under restraint stress (in vivo test)

Wistar strain male rats were employed. Testing drug was administered orally at 10 mg/kg and, after 30 minutes, the restraint stress was given by fixing the forefeet of rat on back side under anesthetization with ether. Moreover, the diameter of pupil (mm) was also measured.

After allowed to stand for 1 hour in separate cage, the defecation level and diameter of pupil were measured.

The inhibitory rate of defecation was determined from following formula.

$$\text{Inhibitory rate (\%)} = \frac{\left(\begin{array}{c}\text{Restrained}\\\text{control group}\end{array} - \begin{array}{c}\text{Nonrestrained}\\\text{group}\end{array}\right) - \left(\begin{array}{c}\text{Drug treat-}\\\text{ment group}\end{array} - \begin{array}{c}\text{Nonrestrained}\\\text{group}\end{array}\right)}{\left(\begin{array}{c}\text{Restrained}\\\text{control group}\end{array} - \begin{array}{c}\text{Nonrestrained}\\\text{group}\end{array}\right)} \times 100$$

Results from above are shown in following table.

|  | In vitro test | | | In vivo test | | |
|---|---|---|---|---|---|---|
|  | $pA_2$ | | | Inhibitory rate of | Diameter of pupil (mm) | |
|  | Ileum | Pupil | Atrium | defecation (%) | Immediately after restraint | After restraint |
| Example 9 | 7.6 | 7.3 | 6.2 | 48.9 | 0.43* | 0.45** |

*Control 0.44,
**Control 0.48

From the results obtained above, the inventive compound exhibited excellent anticholinergic activity and, based on its action, it showed an effect of inhibited defecation level. In addition, the inventive compound exhibited higher selectivity against ileum muscarine receptors than heart muscarine receptors.

Against ileum, in particular, it exhibited the selectivity over 10 times higher than that against atrium of heart. Moreover, it was suggested from in vivo test that it exerted little influence particularly against pupil.

Utilizability in the industry

From the facts above, the compounds of the invention are effective for the treatment of irritable bowel syndrome and the like and are useful as medicinal drugs with high tissue selectivity and less adverse effects on heart and pupil.

We claim:

1. N-substituted pyrrolidine derivatives represented by the general formula (1)

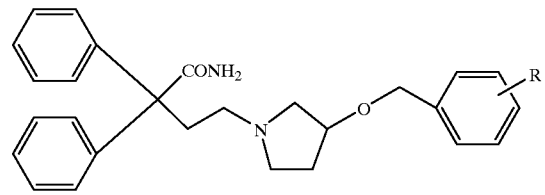

(1)

[wherein R denotes a hydrogen atom, a halogen atom or a lower alkoxy group], and pharmaceutically acceptable salts.

2. A process for preparing compounds represented by the general formula (4)

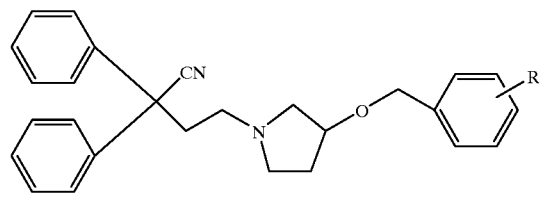

(4)

[wherein R denotes a hydrogen atom, a halogen atom or a lower alkoxy group], characterized by reacting compounds represented by the general formula (3)

(3)

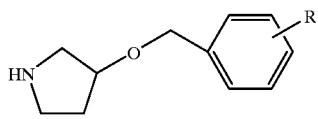

[wherein R is as described above], with compounds represented by the general formula (2)

(2)

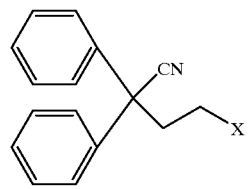

[wherein X denotes a halogen atom].

3. A process for preparing N-substituted pyrrolidine derivatives represented by the general formula (1)

(1)

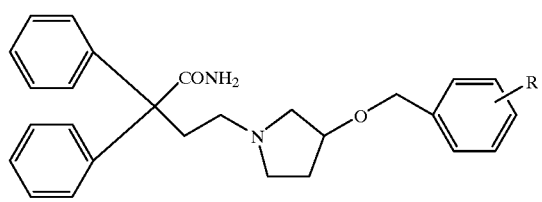

[wherein R denotes a hydrogen atom, a halogen atom or a lower alkoxy group], characterized by hydrolyzing compounds represented by the general formula (4)

(4)

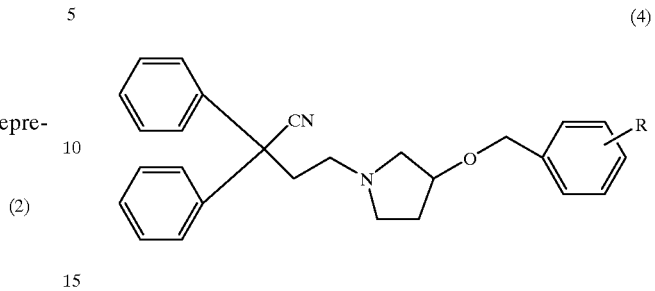

[wherein R is as described above].

4. The compound 4-(3-(3-chlorobenzyloxy)pyrrolidine-1-yl)-2,2-diphenylbutaneamide.

5. A hydrate of the N-substituted pyrrolidine derivative of claim 1.

6. A hydrate of the compound of claim 4.

7. A method for treatment of irritable bowel syndrome in a patient which comprises administering to said patient a therapeutically effective amount of a compound according to claim 1.

* * * * *